United States Patent [19]

Langlois et al.

[11] 4,322,350

[45] Mar. 30, 1982

[54] PROCESS FOR THE SYNTHESIS OF LEUROSINE AND OF ITS DERIVATIVES

[75] Inventors: Nicole Langlois; Yves Langlois, both of Bures; Pierre Potier, Bois-D'ardy, all of France

[73] Assignee: Agence Nationale de Valorisation de la Recherche, Paris, France

[21] Appl. No.: 895,379

[22] Filed: Apr. 11, 1978

[30] Foreign Application Priority Data

Apr. 13, 1977 [FR] France ................. 77 11081

[51] Int. Cl.$^3$ ................................... C07D 519/04
[52] U.S. Cl. .......................................... 260/244.4
[58] Field of Search ...................... 260/287 B, 244.4

[56] References Cited

U.S. PATENT DOCUMENTS 4,144,237  3/1979  Kutney .................... 260/244.4

FOREIGN PATENT DOCUMENTS 1412932  11/1975  United Kingdom .

OTHER PUBLICATIONS

Kutney, et al., (II), Chemical Abstracts, vol. 85, 177744b, (1976).
Costa Noela, et al., Chemical Abstracts, 81, 168875k, (1974).
Padwa, et al., Chemical Abstracts, 79, 31595h, (1973).
Rouchaud, et al., Chemical Abstracts, 76, 59427s, (1972).
Rhone-Poulenc, Chemical Abstracts, 84, 5648m, (1976).
Kruse, et al., Chemical Abstracts, 74, 125286g, (1971).
Neuss, et al., Tetrahedron Letters, No. 7, pp. 783-787, (1968).
Djerassi, Steroid Reactions; An Outline for Organic Chemists, Holden-Day, Inc., San Francisco, (1963), p. 605.
Kutney, et al., (III), Can. J. Chem., vol. 56, No. 1, pp. 62-70, (01/78).
Kutney, et al., Chem. Abst., 85:108873j, (1976).
Langlois et al., Tetrhedron Letters, pp. 3945-3947, Nov. 1976.
Harrison, et al., Compendium of Organic Synthetic Methods, pp. 326-327, (1971).
Morrison, et al., Organic Chemistry, p. 885, (1966).
March, Advanced Organic Chemistry, 1968, p. 618.

*Primary Examiner*—Donald G. Daus
*Assistant Examiner*—Diana G. Rivers
*Attorney, Agent, or Firm*—Maky, Renner, Otto & Boisselle

[57] ABSTRACT

A process for the preparation of a compound of formula (V) and salts thereof

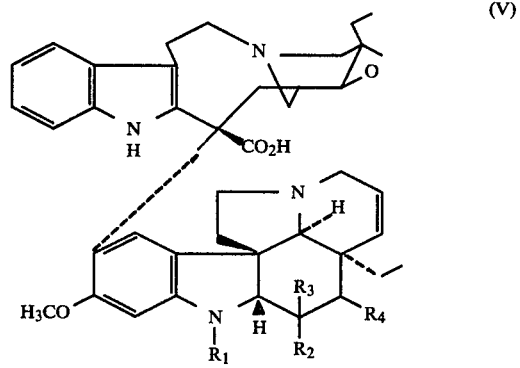

wherein
$R_1$ is selected from the group consisting of a hydrogen atom, an alkyl radical, a formyl radical and an acyl radical;
$R_2$ is selected from the group consisting of an alkoxycarbonyl radical, a hydrazide radical, an acetamido radical, a hydroxymethyl radical, and an alkanoyloxy methyl radical
and
$R_3$ and $R_4$ are the same or different and each is selected from the group consisting of a hydrogen atom, a hydroxyl radical and an alkanoyloxyl radical;
which comprises the step of treating a compound of formula IV

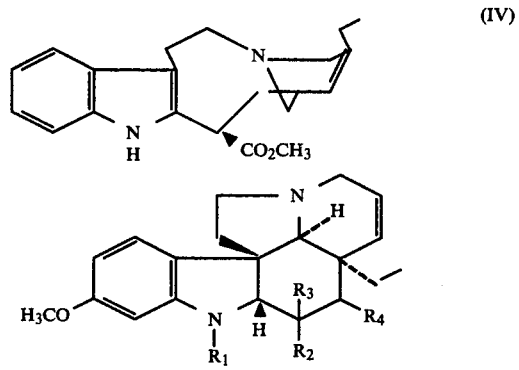

wherein $R_1$, $R_2$, $R_3$ and $R_4$ are as previously defined with at least one oxidising agent selected from the group consisting of oxidising metal salts, air and oxygen.

The above compounds are useful due to their antitumoral activity, and to their use as intermediates of other antitumor drugs.

11 Claims, No Drawings

PROCESS FOR THE SYNTHESIS OF LEUROSINE AND OF ITS DERIVATIVES

The present invention relates to an improvement to the process described in French Pat. No. 74 43221 filed in France on Dec. 31, 1974 in the name of the applicant for the preparation of leurosine.

More particularly, the present invention relates to processes for the preparation of leurosine and of its derivatives from $\Delta^{15'(20')}$dehydroxy-20'-vincaleucoblastine (or "anhydrovinblastine") and its derivatives.

Leurosine corresponding to formula I

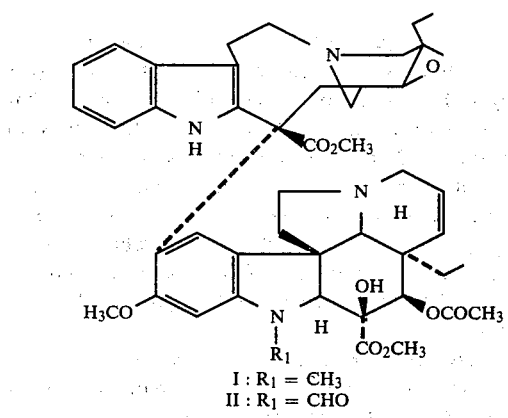

I : $R_1 = CH_3$
II : $R_1 = CHO$ may be isolated from several species of Catharanthus, in particular *C. roseus*. This antitumoral alkaloid is only present in the plant in a small quantity and isolation of it is laborious; it is therefore particularly worthwhile to prepare this compound by hemisynthesis from alkaloids which are abundant and readily available, especially since certain leurosine derivatives (such as Na-demethyl Na-formyl leurosine-formula II: $R_1=CHO$) have noteworthy antitumoral properties.

The process of hemisynthesis described recently in French Pat. No. 74 43221 allows $\Delta^{15'(20')}$ dehydroxy-20'-vincaleucoblastine (or "anhydrovinblastine") corresponding to formula III

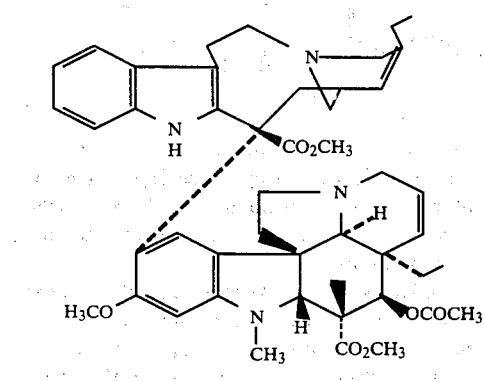

to be prepared from catharanhine and vindoline, and it has been discovered that it may be oxidised to leurosine very economically.

The present invention relates to a process for the preparation of leurosine and of its derivatives corresponding to formula V

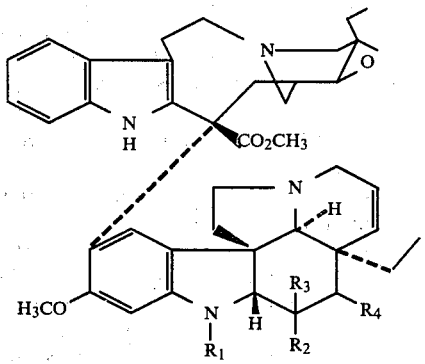

in which $R_1$ represents a hydrogen atom, an alkyl, formyl or acyl radical;

$R_2$ represents an alkyloxycarbonyl, hydrazide acetamido, hydroxymethyl or alkanoyloxymethyl radical;

$R_3$ and $R_4$ represent a hydrogen atom, a hydroxyl or alkanoyloxyle radical; and of its salts, characterised in that a compound corresponding to formula IV

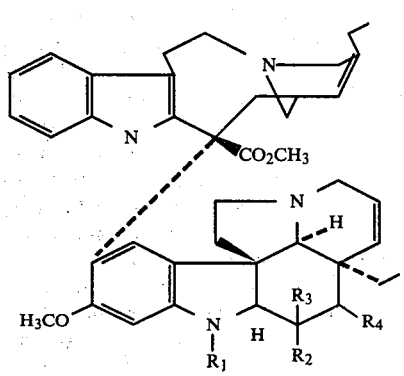

in which $R_1, R_2, R_3$ and $R_4$ have the meanings given above, or one of its salts, is treated with at least one oxidising agent selected from among the oxidising metal salts, air and oxygen.

The alkyl radicals mentioned above are preferably $C_1$ to $C_3$ radicals such as methyl, ethyl and propyl. Similarly, the acyl radicals are preferably $C_1$ to $C_3$ radicals such as the acetyl radical. The alcanoyloxy radicals are preferably $C_1$ to $C_3$ radicals such as the acetyloxy radical.

The starting compounds corresponding to formula IV may be prepared by the process described in the main patent and are preferably compounds in which $R_3$ is a hydroxyl radical, $R_2$ is an acetyloxymethyl radical, $R_4$ is an acetyloxy radical and $R_1$ is the methyl or formyl radical.

In a first method for carrying out the process according to the present invention allowing rapid oxidation, an oxidising metal salt such as lead tetraacetate or thallium triacetate is reacted on the compound corresponding to formula IV in solution in an organic solvent, in particular a chlorinated hydrocarbon such as methylene chloride or chloroform, and aromatic hydrocarbon such as benzene, or an ester such as ethyl acetate, preferably in an inert atmosphere, for example under nitrogen or argon, at low temperature, for example between $-15°$ and $15°$ C. In this first method for carrying out the process, the oxidation reaction generally lasts less than one hour.

In a second method for carrying out the process according to the present invention, air or oxygen is reacted on the compound corresponding to formula IV, either in solution in a solvent as above, or in a ketone such as acetone, or adsorbed on a solid support such as an adsorbent for chromatography. In the second method of carrying out the process, the reaction may be catalysed by a transition metal, for example nickel, palladium or platinum, or a salt of this metal. When carrying out the process, it is advantageous to perform oxidation by air or oxygen in a solvent in the presence of an adsorbent such as silica or alumina. This second method of carrying the invention leads to a longer oxidation period, generally between 24 and 72 hours, but the reaction may be carried out at ambient temperature.

The product of oxidation obtained by the process according to the present invention contains, in addition to the compound corresponding to formula V, a proportion of the compound corresponding to formula IV which has not reacted and which may be recycled after separation.

Separation is carried out by any known process such as thick layer chromatography starting from an organic phase containing the mixture of compound V and IV.

In a preferred method of carrying out the process according to the present invention, a solution of the compound corresponding to formula IV in a solvent preferably selected from among chloroform, methylene chloride, ethyl acetate or acetone is stirred in the presence of silica or alumina under an air stream or under an oxygen atmosphere preferably for 48 to 72 hours at a temperature preferably selected between $10°$ and $50°$ C. The process according to the present invention thus leads, after filtration and evaporation of the solvent under reduced pressure, to a mixture of leurosine I or of a derivative corresponding to general formula V and of "anhydrovinblastine" III or of a derivative corresponding to general formula IV which may be recycled. The desired product is separated by known methods, in particular by chromatography.

The examples below are intended to illustrate the invention but do not limit it in any way.

EXAMPLE 1

A solution of 28 mg of lead tetraacetate in 2 cm³ of methylene chloride is added to a solution of 50 mg of "anhydrovinblastine" III in 3 cm³ of methylene chloride kept under argon at 0° C. with stirring. The reaction medium is left with stirring at 0° C. for 15 minutes then taken up by 20 cm³ of chloroform and 5 cm³ of a dilute aqueous solution of sodium carbonate. The aqueous phase is extracted for a further three times by 15 cm³ of chloroform. The combined organic phases are washed with 10 cm³ of distilled water, dried on sodium sulphate and filtered. The solvent is eliminated by evaporation under reduced pressure (15 mm Hg) at 30° to 40° C. The mixture obtained which has been purified by chromatography on a thick layer of silica (eluant: ethylacetate/absolute ethanol 75/25), provides 16 mg of leurosine I and 17.5 mg of "anhydrovinblastine" III.

EXAMPLE 2

A solution of 50 mg of "anhydrovinblastine" III in 3 cm³ of chloroform at ambient temperature (20° C.) is stirred in the air in the presence of 50 mg of silica for 72 hours then diluted with 20 cm³ of chloroform/methanol 85/15 mixture, filtered and evaporated under reduced pressure. The mixture obtained is purified by chromatography on a thick layer of silica under the same conditions as in Example 1 and provides 13.8 mg of leurosine I and 20 mg of "anhydrovinblastine" III which may be recycled.

EXAMPLE 3

A solution of 36 mg of "ahydrovinblastine" III in 0.3 cm³ of acetone is adsorbed on 360 mg of alumina (for thin layer chromatography) and left in the air at ambient temperature for 24 hours. The mixture is then stirred in the presence of 2 cm³ of acetone for 24 hours at ambient temperature. The adsorbent is filtered and rinsed and the solvent is separated under reduced pressure. The leurosine formed (8.5 mg) is separated by chromatography on a thick layer of silica (eluant: chloroform/methanol 95/5) from the remaining "anhydrovinblastine" (9.6 mg).

The products obtained by this process are useful either as drugs or as intermediaries in the preparation of drugs particularly for antitumoral action.

We claim:

1. A process for the preparation of a compound of formula (V) and salts thereof

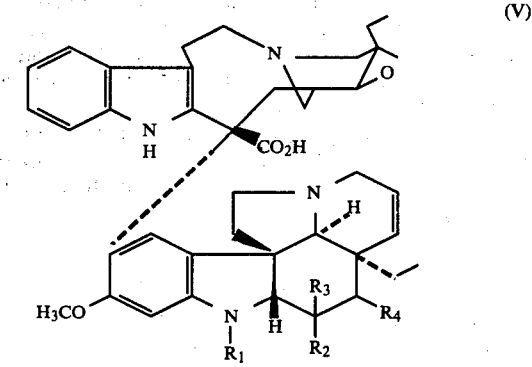

(V)

wherein
- $R_1$ is selected from the group consisting of a hydrogen atom, an alkyl group having 1 to 3 carbon atoms, a formyl group and an acyl group having 1 to 3 carbon atoms;
- $R_2$ is selected from the group consisting of an alkoxycarbonyl group, a hydrazide group, an acetamido group, a hydroxymethyl group, and an alkanoyloxy methyl group, and wherein the alkoxy and alkanoyl groups have 1 to 3 carbon atoms; and
- $R_3$ and $R_4$ are the same or different and each is selected from the group consisting of a hydrogen atom, a hydroxyl group and an alkanoyloxyl group having 1 to 3 carbon atoms;

which comprises the step of oxidizing a compound of formula IV

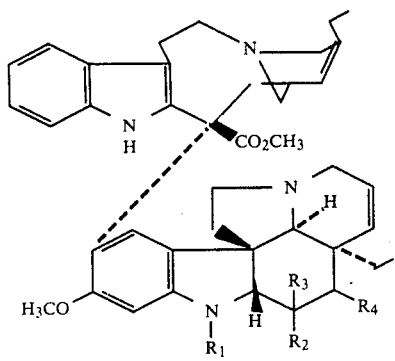 (IV)

wherein $R_1$, $R_2$, $R_3$ and $R_4$ are as previously defined with at least one oxidizing agent selected from the group consisting of lead tetraacetate, thallium triacetate, air, and oxygen.

2. A process according to claim 1 wherein the oxidising agent is an lead tetraacetate or thallium triacetate.

3. A process according to claim 2, wherein the reaction is carried out in a solvent selected from the group consisting of chlorinated hydrocarbons, aromatic hydrocarbons and esters.

4. A process according to claim 3, wherein the reaction is carried out in a solvent selected from the group consisting of methylene chloride, chloroform, benzene and ethyl acetate.

5. A process according to claim 2, wherein the reaction is carried out at a temperature of between $-15°$ and $15°$ C.

6. A process according to claim 2, wherein the reaction is carried out in an inert atmosphere.

7. A process according to claim 1, wherein the oxidising agent is air or oxygen.

8. A process according to claim 7, wherein the reaction is carried out in a ketone solvent.

9. A process according to claim 7, wherein the reaction is carried out in a solvent selected from the group consisting of methylene chloride, chloroform, benzene, ethyl acetate and acetone.

10. A process according to claim 7 wherein the reaction is carried out in the presence of silica or alumina.

11. A process according to claim 7, wherein the compound corresponding to formula IV is adsorbed on a solid support.

* * * * *